(12) United States Patent
Loeb (10) Patent No.: US 7,885,714 B2
(45) Date of Patent: Feb. 8, 2011

(54) COCHLEAR IMPLANT FITTING

(75) Inventor: Gerald E. Loeb, South Pasadena, CA (US)

(73) Assignee: University of Southern California, Los Angeles, CA (US)

(*) Notice: Subject to any disclaimer, the term of this patent is extended or adjusted under 35 U.S.C. 154(b) by 453 days.

(21) Appl. No.: 11/469,357

(22) Filed: Aug. 31, 2006

(65) Prior Publication Data

US 2007/0129772 A1 Jun. 7, 2007

Related U.S. Application Data

(60) Provisional application No. 60/713,247, filed on Sep. 1, 2005.

(51) Int. Cl.
*A61N 1/00* (2006.01)
(52) U.S. Cl. .................................................. 607/57
(58) Field of Classification Search .................. 607/57
See application file for complete search history.

(56) References Cited

U.S. PATENT DOCUMENTS

| | | | |
|---|---|---|---|
| 6,219,580 B1 | 4/2001 | Faltys et al. | |
| 6,289,247 B1 | 9/2001 | Faltys et al. | |
| 6,308,101 B1 | 10/2001 | Faltys et al. | |
| 6,600,955 B1* | 7/2003 | Zierhofer | 607/57 |
| 7,076,308 B1* | 7/2006 | Overstreet et al. | 607/57 |
| 7,171,272 B2* | 1/2007 | Blamey et al. | 607/57 |
| 7,251,530 B1* | 7/2007 | Overstreet et al. | 607/55 |
| 2005/0107843 A1* | 5/2005 | McDermott et al. | 607/57 |
| 2005/0261748 A1* | 11/2005 | van Dijk | 607/57 |
| 2007/0179565 A1* | 8/2007 | Overstreet et al. | 607/57 |
| 2008/0033507 A1* | 2/2008 | Litvak et al. | 607/57 |

FOREIGN PATENT DOCUMENTS

| | | |
|---|---|---|
| WO | WO 03/099179 A1 | 12/2003 |
| WO | WO 2004/021363 A1 | 3/2004 |

OTHER PUBLICATIONS

Anderson DJ et al., Temporal position of discharges in single auditory nerve fibers within the cycle of a sine-wave stimulus: frequency and intensity effects, The Journal of the Acoustical Society of America, Apr. 1971, pp. 1131-1139, vol. 49 (4B), Acoustical Society of America, New York.

(Continued)

*Primary Examiner*—Niketa I Patel
*Assistant Examiner*—Rex Holmes
(74) *Attorney, Agent, or Firm*—McDermott Will & Emery LLP (57) ABSTRACT

Systems and methods for fitting cochlear implants. The cochlear implant fitting systems and methods can be used to generate various stimulus patterns for fitting patients with speech processors for cochlear implants. The fitting systems and methods provide means to identify rapidly which of several speech processing strategies could function effectively in cochlear implant patients.

24 Claims, 4 Drawing Sheets

OTHER PUBLICATIONS

Eddington DK et al., Auditory prostheses research with multiple channel intracochlear stimulation in man, Nov.-Dec. 1978;87(6 Pt 2):1-39, Ann Otol Rhinol Laryngol., St. Louis, MO.

Sachs, MB et al. Effects of nonlinearities on speech encoding in the auditory nervea, The Journal of the Acoustical Society of America, Sep. 1980, pp. 858-875, vol. 68 (3), Acoustical Society of America, New York.

Loeb GE et al., Spatial cross-correlation: a proposed mechanism for acoustic pitch perception, Biological Cybernetics, 1983, vol. 47, pp. 149-163, Springer-Verlag, New York.

Shannon RV, Multichannel electrical stimulation of the auditory nerve in man. 11. Channel interaction, Hearing Research, 1983, pp. 1-16, vol. 12, Elsevier, New York.

Kiang NY et al., Discharge patterns of single fibers in the cat's auditory nerve, Feb. 1996, pp. 28-31, 73-81, 87-89, 96-107, 112-113, 118-131, 145-151, The MIT Press, Cambridge, MA.

Bierer JA et al., Cortical responses to cochlear implant stimulation: channel interactions, Journal of the Association for Research in Otolaryngology, Jul. 28, 2003, pp. 32-48, vol. 5, Springer, New York.

Kessler, D.K. "The Clarion Multi-Strategy Cochlear Implant," Annals of Otology, Rhinology & Laryngology, Apr. 1999, Suppl. 177, vol. 108, No. 4, Part 2, pp. 8-16.

Koppl C. "Phase Locking to High Frequencies in the Auditory Nerve and Cochlear Nucleus Magnocellularis of the Barn Owl, Tyto alba," J. Neurosci., May 1, 1997, vol. 17, No. 9, pp. 3312-3321.

Wilson B.S. et al. "Design and Evaluation of a Continuous Interleaved Sampling (CIS) Processing Strategy for Multichannel Cochlear Implants," Journal of Rehabilitation Research and Development, 1993, vol. 30, No. 1, pp. 110-116.

EPO Examination Report for EPO Application No. 06802893.5, dated Sep. 10, 2009.

* cited by examiner

COCHLEAR IMPLANT FITTING

CROSS REFERENCE TO RELATED APPLICATIONS

This patent application is related to and claims the benefit of the filing date of U.S. provisional application Ser. No. 60/713,247, filed Sep. 1, 2005, entitled "Cochlear Implant Fitting," including Exhibit A thereto, entitled "Cochlear Implants and Perceptual Dissonance," the contents of all of which are incorporated herein by reference.

BACKGROUND OF THE INVENTION

1. Field

This application relates generally to systems and methods for calibrating and fitting cochlear implants.

2. Related Art

A cochlear implant is a device that may be surgically implanted into a person's cochlea to stimulate it to cause hearing. It may include a tiny receiver which is placed under the skin in the bony part behind the ear. The receiver may have a probe with several electrodes that is implanted into the cochlea. A cochlear implant can be useful if the hearing loss is caused by problems with the cochlea (usually damaged hair cells) or where the loss is caused by problems with the middle ear that cannot be corrected.

A person with a cochlear implant may also wear a hearing aid like device that has a microphone, a processor and a transducer. The processor may manipulate what the microphone hears and may send a signal to the transducer, which may be worn just behind the ear. The transducer may change the signal from an electrical signal to a magnetic signal that can be received through the skin by the implanted receiver. The receiver may then stimulate the probe in the cochlea causing the person to hear.

Great variability in preferences for and performance with various speech processing strategies in cochlear implant patients may arise from inherent and/or learned differences in the way that individuals interpret conflicting cues about pitch. Modern cochlear implants support multiple speech processing strategies (such as the CLARION family of implants from Advanced Bionics Corp.) in order to improve the chances of finding one that provides satisfactory hearing for the patient. Each strategy may require multiple fitting parameters to be determined through interactive psychophysical tests. The whole fitting process can be difficult and tiresome for the patient and time-consuming to the audiologist who adjusts the parameters and administers the tests. It may not even be immediately obvious which strategy works best for the patient. This may instead require a prolonged period of use and learning with each strategy to obtain a meaningful comparison.

As cochlear implant technology has developed, the numbers and ranges of parameters that may be set have increased greatly. The CLARION II implant has 16 independently and simultaneously programmable current sources whose output levels can be changed in less than 2 μs. Its external speech processor can digitally filter sound input into 32 or more frequency bands, each of which can be mapped to virtually any combination of electrodes and stimulus waveforms. Sounds can be represented as simultaneous analog waveforms, interleaved biphasic waveforms, or various combinations of overlapping waveforms called "virtual channels". The repetition rate of pulsatile stimulation can exceed 20 kpps on each electrode. Any and all of these parameters may control the nature of the sound perception in patients, but often in ways that are unpredictable and difficult to correlate with their preferences and performance with particular speech processing strategies. An exhaustive search of the parameter space may be impractical.

The growing heterogeneity of ad hoc strategies and cognitive performance suggests that electrical stimulation may produce un-physiological effects on a neural mechanism for pitch perception that is different from the place-pitch and rate-pitch mechanisms on which cochlear implants have been based (see below). This may result in perceptual dissonance that subjects resolve in different ways. Until that unknown mechanism is identified and controlled, the evolution of cochlear implants may be frustratingly empirical and fragmented. Indeed, recent tests of new and "improved" strategies based on classical theories of auditory perception can confound predictions, and may produce inconsistent results at best.

SUMMARY

The embodiments of cochlear implant fitting systems and methods described herein are merely exemplary and can be used to generate various stimulus patterns for fitting patients with speech processors for cochlear implants.

Embodiments of the cochlear implant fitting systems and methods provide means to identify rapidly which of several speech processing strategies could function effectively in cochlear implant patients. Exemplary embodiments comprise computational devices programmed to produce a particular class of electrical stimulation patterns that can be delivered to the auditory nerve of a patient via his/her cochlear implant. Exemplary systems comprise a processor with a user interface and controller for controlling the operation of a cochlear implant and its electrode array.

BRIEF DESCRIPTION OF THE DRAWINGS

Aspects of the biomedical stimulation devices and systems are illustrated by way of example, and not by way of limitation, in the accompanying drawings, wherein.

DETAILED DESCRIPTION

The detailed description set forth below in connection with the appended drawings is intended as a description of exemplary embodiments and is not intended to represent the only embodiments in which the biomedical stimulation devices, methods and systems can be practiced. The term "exemplary" used throughout this description means "serving as an example, instance, or illustration," and should not necessarily be construed as preferred or advantageous over other embodiments. The detailed description includes specific details for the purpose of providing a thorough understanding of the biomedical stimulation devices, methods and systems. However, it will be apparent to those skilled in the art that the biomedical stimulation devices, methods and systems may be practiced without these specific details.

Embodiments of the cochlear implant fitting systems and methods provide means to identify rapidly which of several speech processing strategies could function effectively in cochlear implant patients. Exemplary embodiments comprise computational devices programmed to produce a particular class of electrical stimulation patterns that can be delivered to the auditory nerve of a patient via his/her cochlear implant. The patient can provide information to describe features of the sound percepts that he/she experiences in response to the stimulation patterns. This information can indicate to the audiologist which speech processing strategy or particular settings of a strategy to try with the patient. The cochlear implant fitting systems and methods can be used with a variety of cochlear implants known to those skilled in the art, such as, for example, those described in U.S. Pat. Nos. 6,219,580 to Faltys et al.; 6,308,101 to Faltys et al.; and 6,289,247 to Faltys et al.; the contents of each of which are incorporated herein by reference.

Figure 1:
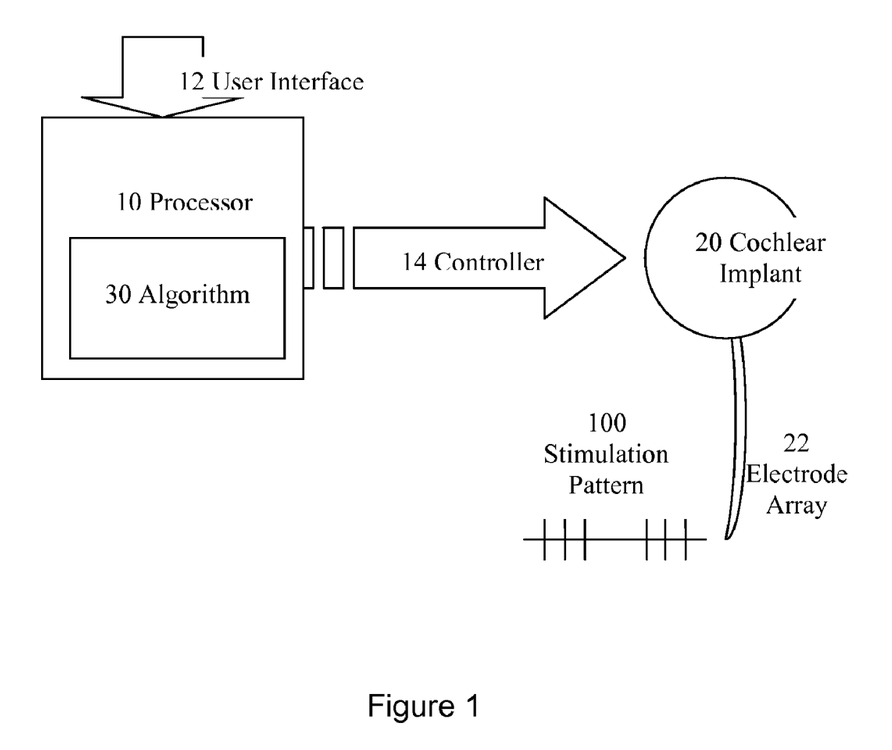
FIG. 1 is a schematic diagram of a cochlear implant fitting system.
Figure 2:
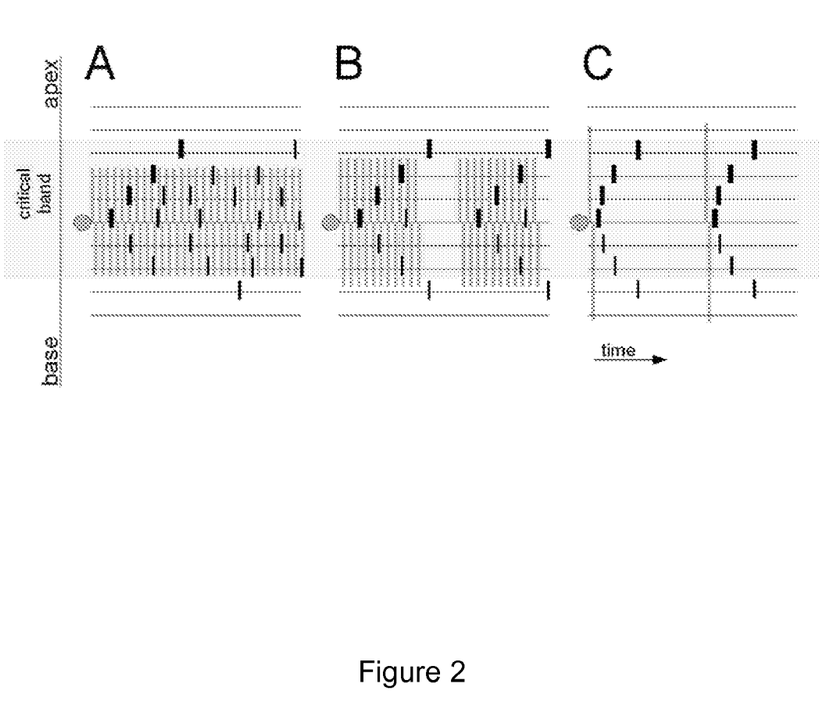
FIG. 2 is a schematic representation of the phasing of neural unit activity anticipated in response to interrupted trains of high frequency biphasic stimulation.

The exemplary embodiment schematically illustrated in FIG. 1 comprises a processor 10 with user interface 12 and controller 14 for controlling the operation of cochlear implant 20 and its electrode array 22. Processor 10 comprises program 30 which enables a user to cause cochlear implant 20 to generate any of a class of electrical stimulation patterns 100 on its electrode array 22. The class of electrical stimulation patterns 100 is illustrated graphically in FIG. 2. FIG. 2 shows a schematic representation of the phasing of neural unit activity anticipated in response to interrupted trains of high frequency biphasic stimulation as indicated by the light gray waveforms in FIG. 2B, compared to continuous high frequency stimulation in FIG. 2A and single pulses at the interruption frequency in FIG. 2C (vertical axis=place, extent ~2 mm; horizontal axis=time, arrow ~250 µs). Stimulus amplitudes are adjusted to produce equal extent of firing and equal loudness in all panels. FIG. 2A shows a high frequency train of very short biphasic pulses (e.g. 10 µs/phase @ 20 kHz); there is a coherent phase at the start of the train but it rapidly randomizes if the train is continuous. FIG. 2B shows the same high frequency carrier as FIG. 2A but divided into bursts. FIG. 2C shows individual biphasic pulses at the same rate as the burst frequency in FIG. 2B.

In an exemplary embodiment, the frequency of stimulation could be sufficiently high so as to preclude phase-locking of auditory nerve activity at the stimulus frequency, i.e. >4 kpps. The stimulation frequency can be interrupted at intervals less than those associated with rate pitch sensations, i.e. <3 ms, but greater than those associated with phase-locking, i.e. >0.3 ms. The duration of the interruption can be varied over the entire range of afforded by the relationship between the stimulation frequency and the interruption interval. For example, a 20 kpps stimulation frequency interrupted at 1 ms intervals could consist of individual trains ranging from 19 pulses with one omitted pulse down to 1 pulse with 19 omitted pulses. The percepts of pitch and timbre (i.e. sound quality) can be compared between different patterns of interrupted stimulation, which may include the pattern having no interruptions (FIG. 2A) and the pattern having only interruptions and no representation of the stimulation frequency (FIG. 2C).

The class of electrical stimulation patterns 100 can include additional variations. For example, similar patterns could be administered at the same frequency to two or more electrodes at the same time but with different signs and/or amplitudes of stimulation on each electrode. Also, similar patterns could be administered at the same frequency to two or more electrodes at the same time but with phase delays between electrodes. Alternatively, similar patterns could be administered at the same frequency to two or more electrodes at the same time but with different stimulus waveforms on each electrode.

Mechanisms for encoding pitch can be identified by examining temporospatial patterns of activity in the population of cochlear nerve activity. This has resulted in three generally accepted and essentially orthogonal encoding mechanisms: place-pitch, rate pitch, and a poorly understood "phase-locked" pitch. While cochlear implants have been traditionally designed based upon the place-pitch and rate-pitch theories, exemplary embodiments of the present Cochlear implant systems and methods additionally address the phase-locking of auditory nerve activity to both acoustic and electrical stimulation. Systematic means to control these putative phase effects using modern, high-speed and high-density cochlear implants may make it possible to identify more efficiently the best strategy for a given patient and to minimize the perceptual confusion that arises from conflicting sensory cues.

Place pitch, based on the spectral filtering properties of the basilar membrane, operates over the entire range of audible frequencies but has substantial problems with accuracy and precision over the wide dynamic range of sound intensity and perceived loudness. That is because the spatial filters are highly nonlinear and asymmetrical. Neural spike activity tends to saturate and its distribution shifts basally as the amplitude of a single tone increases. If two closely spaced frequencies are presented together, there are distortion products in the basilar membrane motion and nonlinear summation in the neural activity. Somehow the brain corrects for this distortion or suppresses the inaccurate information entirely to give rise to the remarkable constancy of pitch perception over a very wide dynamic range of loudness and musical intervals.

Rate pitch is akin to the sense of tactile vibration. It operates only at frequencies for which individual neurons can generate cycle-by-cycle action potentials, a capability that declines sharply in the auditory nervous system above 300-500 Hz (Rose, 1970). However, rate information probably is encoded and decoded from everywhere along the basilar membrane because most naturally occurring acoustic sources are composed of overtones of fundamental frequencies that lie within the rate pitch range. The envelope of the higher overtones tends to be amplitude modulated at the fundamental frequency. The pitch ascribed to an electrical stimulation train by a cochlear implant subject tends to be related to the frequency of stimulation at low frequencies (~100 pps) but becomes dominated by place of stimulation at $\geq$300 pps (Zeng, 2002).

Phase-locked pitch is an encoding mechanism in search of a decoding mechanism (see, for example, Loeb, G. E., White, M. W., & Merzenich, M. M. (1983). *Spatial cross-correlation. A proposed mechanism for acoustic pitch perception*. Biological Cybernetics, 47, 149-163, incorporated herein by reference). Over the frequency range that is critical for speech perception (300-3000 Hz), auditory neurons tend to generate their action potentials in phase with basilar membrane motion but at random subharmonics that lie within their limited range of firing rates (see, for example, FIG. 4.7 in Kiang, N. Y. S. (1965). *Discharge Patterns of Single Fibers in the Cat's Auditory Nerve*. MIT Research Monographs, 35; and Anderson, D. J., Rose, J. E., Hind, J. E., & Brugge, J. F. (1971). *Temporal position of discharges in single auditory nerve fibers within the cycle of a sine-wave stimulus: frequency and intensity effects*. Journal of the Acoustical Society of America, 49, 1131-1139; the contents of each of which are incorporated herein by reference). By combining the trains of action potentials from an ensemble of such phase-locked neurons at a single location on the basilar membrane, the frequency of pitches well above the rate-pitch range could be represented in the frequency of the composite "volley" of action potentials.

Figure 3:
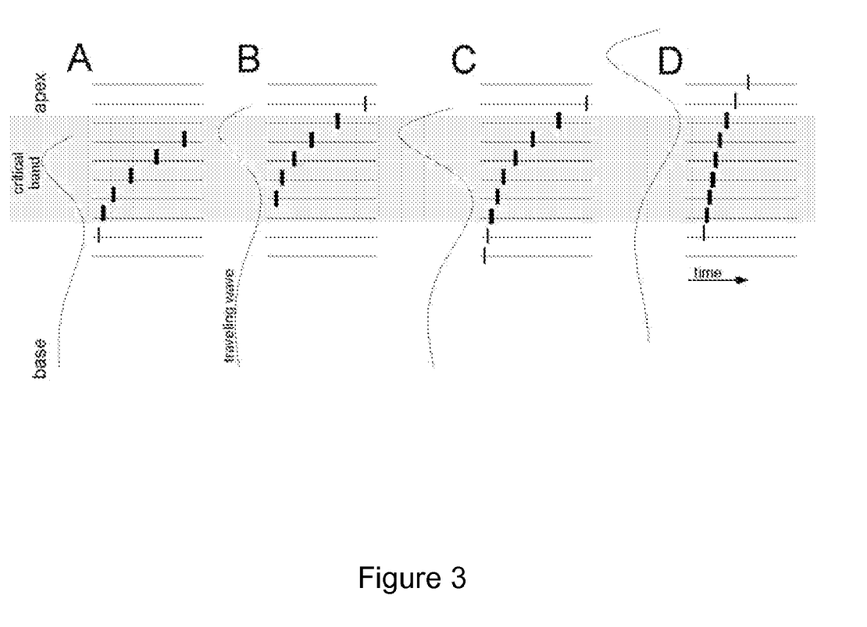
FIG. 3 is a schematic representation of the phasing of neural unit activity as a function of distance along the cochlea.

In the highly evolved mammalian cochlea with its systematic gradient of mechanical properties, coherent mechanical amplification by the outer hair cells results in the abrupt slowing of the traveling wave at the point of resonant tuning. As depicted schematically in FIG. 3A, spiral ganglion cells that are phase-locked to basilar membrane motion can have the steepest and most rapidly changing spatial gradient of phase for the locally resonant frequency. Much shallower and more constant phase gradients can occur at the same location for lower frequencies that have sufficient amplitude to excite these ganglion cells as they pass through to their more apical tuning point (FIGS. 3B-D). Increases in acoustic amplitude of a given frequency tend to saturate the firing rates of ganglion cells from progressively larger regions extending basally but they do not change the phase gradients (FIGS. 2B and 3C). Closely spaced harmonics tend not to be resolvable based on mean firing rates at moderate loudness, whereas abrupt phase transitions persist at the resonant place for each harmonic. These phase shifts persist even when the adjacent harmonics are more intense and dominate the phase-locking itself. If the local phase gradient could be extracted from the phase-locked discharge of the spiral ganglion cells, it would provide the information required to account for the remarkable stability of pitch vs. loudness at frequencies around 1-3 kHz and for the otherwise paradoxical improvement in frequency discrimination with increasing loudness.

When multiple, closely spaced acoustic frequencies are combined on the basilar membrane, the regions of phase-locking to a single frequency tend to be about one critical band long (~1 mm; see for example, Sachs, M. B. & Young, E. D. (1980). *Effects of nonlinearities on speech encoding in the auditory nerve*. Journal of the Acoustical Society of America, 68, 858-875; the contents of which are incorporated herein by reference), which corresponds to the smallest frequency spacing that is perceived as a musical interval rather than as timbre when two notes are played simultaneously (the major second; two semitones). Thus the phase-locked pitch decoding mechanism may operate over basilar membrane distances $\leq 1$ mm but long enough to experience a substantial phase gradient (at least 90°). This relatively short distance would account for the absence of discernible effects from changes in the sequencing of stimulation in multichannel cochlear implants (i.e. basal-to-apical, reversed or random). Even the closest spaced electrodes (0.8 mm in Nucleus® implants) are near the limits of spatial cross-correlation and such electrodes produce massive channel interaction when adjacent contacts are activated even in an interleaved temporal pattern (Shannon, 1983; Eddington et al., Reference Note 10; Bierer & Middlebrooks, 2004).

The neural decoder could operate as an ensemble of short-distance cross-correlators covering the range of phase-locked frequencies (~300-3000 Hz). By including delays, inhibitory synapses or local dendritic circuits for synaptic gating, it is possible to create ensembles that represent component pitches as peaks, valleys, edges, etc. in the neural population. As illustrated schematically in FIG. 3), one of the most salient cues appears to be the second derivative of phase. At the characteristic place (FIG. 3A), a tonal stimulus would result in a convergence of high levels of neural activity (to be decoded as place pitch) and maximal phase acceleration (to be decoded as phase-locked pitch). A slightly lower pitched tonal stimulus with high loudness (FIG. 3C) could produce similar place-related activity (because of saturation) but would have a significantly lower phase acceleration over this range of CFs. A much lower pitched tonal stimulus (FIG. 3D) could produce a much flatter phase gradient but the nervous system might not use this information to influence pitch judgment because its place pitch is located much more apically.

The patterns that are actually extracted by the ensemble of cross-correlators are closely related to the pitches that could be extracted by a simple place-pitch decoder for the corresponding pure tones. This makes it feasible for the nervous system to learn associations during the development of speech and hearing. Conversely, this tendency makes it difficult to test hypotheses about phase-pitch extraction using acoustic stimuli and psychophysical measurements. If the nervous system does, indeed, learn these associations rather than having them wired in genetically, this has important implications for congenitally deaf recipients of cochlear implants. In particular, some of the experiments suggested in Exhibit A, entitled "Cochlear Implants and Perceptual Dissonance," (which was attached to provisional application Ser. No. 60/713,247, entitled "Cochlear Implant Fitting," to which this application claims priority and which is incorporated herein by reference in its entirety) may produce different results in such patients (although they may lack the vocabulary to describe their percepts in the same way as post-linguistically deafened patients).

Using Advanced Cochlear Implants to Identify the Phase-Locked Pitch Decoder

When the phase-locked pitch paradox was first identified in cochlear implant recipients, the technology was too primitive to provide fine enough control over temporospatial patterns of neural activity to be able to distinguish among possible pitch-decoding algorithms. Modern cochlear implants now have electrode contacts spaced approximately by a critical band and they permit very precise timing of independently controlled stimulus waveforms on multiple, adjacent contacts. For example, the CLARION CII provides ~1 μs resolution for arbitrary waveforms including biphasic pulse rates >100 kpps. The effects of current spread and cross-talk between adjacent contacts, however, make it difficult to recreate directly the local temporospatial details of natural phase-locking to the acoustic traveling wave. Nevertheless, electrical stimulation patterns can be designed that have noticeable and consistent effects on the perception of pitch and/or timbre. Systematic psychophysical studies of these effects could then be used to identify at least the broad outlines of the decoding algorithm used by the brain. That, in turn, could lead to the systematic design and selection of speech processing and stimulation strategies that reduce the perceptual dissonance that may be confusing many cochlear implant recipients.

High frequency pulsatile stimulation provides a unique opportunity to separate the effects of place and phase-locked gradients (FIG. 2). Symmetrical biphasic pulses were originally suggested for CIS because theoretically they should produce no residual membrane depolarizations in neurons that have not reached threshold for action potential initiation. However, membrane channels produce some rectification at subthreshold potentials, resulting in modest, residual polarization that contributes to undesirable crosstalk among adjacent sites of cochlear stimulation. The effects of residual depolarization and summation have been observed as relatively weak cross-talk between nearby electrodes even with relatively long duration biphasic pulses (80 μs/phase) at low frequencies (250 pps) for interleaving delays up to 640 μs. The solution to this is asymmetrical triphasic waveforms, which can be tuned to cancel these residual effects and reduce crosstalk.

In order to achieve very high pulse rates, it can be beneficial to use very brief pulse widths. Under these conditions, the residual depolarization produced by biphasic pulses can become the dominant mode of stimulation. The same biophysical theory that suggested the use of balanced biphasic stimulation (e.g. CIS strategy) predicts that threshold currents for such narrow pulses should rise at least to preserve constant charge (and even more steeply to compensate for the activation time of voltage-dependent sodium channels). If there were no residual depolarization of subthreshold neurons, then decreases in interpulse interval beyond the absolute refractory period (~1 ms) should have little or no effect on neural recruitment. In fact, the thresholds for trains of narrow biphasic pulses continue to decline with pulse rate over the entire range from 200 to at least 6000 pps. That is because the effective stimulus is the nonzero net transmembrane current from each extracellular biphasic pulse, which is the equivalent of intracellular monophasic current pulses. Interpulse intervals of less than 1 ms presumably permit integration of these monophasic current pulses by the spiral ganglion cells, which have time constants in this range (Loeb, White & Jenkins, 1983). This suggests that the low thresholds obtained at high repetition rates are likely to be accompanied by a substantial increase in cross-talk among nearby channels (thereby defeating the original reason for changing from analog stimulus waveforms to CIS strategies).

Figure 4:
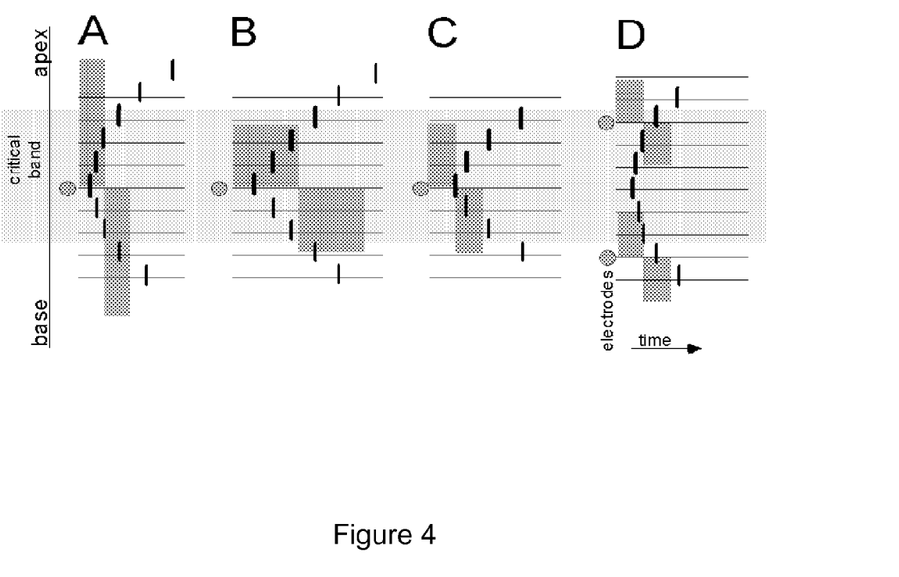
FIG. 4 is a schematic representation of the phasing of neural unit activity similar to FIG. 3.

Once the frequency of biphasic stimulation becomes high enough (>5 kpps), the spiral ganglion cells will no longer phase-lock to the individual pulses but will phase-lock instead to modulations of this carrier. At the onset of the carrier, this should result in phase gradients similar to those that would be produced by integration during the first phase of an infinitely long duration pulse; i.e. the neurons closest to the stimulation site would fire earlier in the high frequency train than those further away, which would need to integrate more of the weaker residual depolarization effects that they receive. Note, however, that this phasing would rapidly randomize in the case of a continuous high frequency train of narrow pulses. Such pulses provide the equivalent of a continuous depolarizing current, which would cause each neuron independently to integrate, fire and reset asynchronously (FIG. 2A). Thus the pitch associated with such a train will be dominated by the place pitch alone, with no conflicting information from rate or phase-locked pitch cues. Repetitive bursts of high frequency pulses (FIGS. 2B, 2C) will allow phase-locking to recur at the start of each burst if the pauses between them are long enough for a substantial decay of membrane depolarization. The shape of the phase gradients will then depend on the duration of the bursts and the intensity of the stimulation, just as it does for the longer biphasic pulses of the CIS strategy, as illustrated in FIG. 4.

If the repetition rate of bursts of high frequency pulses is high enough to eliminate any rate-pitch cues (>500-1000 Hz depending on subject), then pitch differences between the carrier bursts and the continuous carrier may be attributed to the phase-locked pitch decoder. A phase gradient with a high acceleration (such as produced by including only one pulse per burst; see FIG. 2C, similar to FIG. 4A) would be closest to the condition for acoustical stimuli at the characteristic frequency of the place (e.g. FIG. 3A), so this stimulus should provide a strong reinforcement of the place pitch and it should sound the most like a pure tone when compared to the continuous carrier. A phase gradient with less acceleration (e.g. FIG. 2B) would normally be associated with a traveling wave tuned somewhat more apically (e.g. FIG. 3B, 3C), so it should be perceived at a lower pitch (up to 1-2 semitones) and perhaps less tone-like than percepts produced by more conventional biphasic pulse trains at frequencies <1 kpps. A phase gradient that is too flat would tend to be ignored because it would normally be associated with a characteristic frequency at an apical place beyond a critical band away (e.g. FIG. 3D). Note that the random-phase condition in FIG. 2A is very different from a coherent phase with a flat gradient such as FIG. 4D, but it might be interpreted similarly by the local neural decoder. However, the typical to produce the flat gradient at one place is to stimulate at high intensity, which may produce a spread of excitation in both directions plus a steep phase gradient at the fringes.

Another methodological tool could be built on the virtual channel strategy, which allows the place-pitch centroid to be steered continuously between the available electrode contact positions. This can be been done by stimulating two adjacent electrodes so as to create a peak of current density that lies between the two sites. It is also possible to create virtual channels located outside the interval defined by the electrode positions by applying antiphasic stimulation currents, effectively summing the cathodal phase of one stimulation site with the virtual cathode that tends to be created at a distance from the anodal phase of the other site. As with typical electrical stimulation, paired stimuli seem likely to create orderly gradients of action potential initiation whose spatial slope should depend on stimulus pulse duration and intensity (indicated speculatively in FIG. 4D). The shape of these gradients could be further influenced by introducing small phase delays or shape differences between the two stimuli, an experiment that has yet to be performed systematically. The CLARION CII architecture includes multiple stimulus channels that can apply independently controlled stimulus currents simultaneously to multiple electrode contacts. Its 1 μs temporal resolution is much faster than the likely sensitivity of the neural decoder for phase-locked pitch, which is estimated to be about 20 μs.

The actual temporospatial patterns of action potential generation could be difficult to predict for a particular stimulation train in a given cochlear implant recipient. They arise from the non-intuitive interaction of many different stimulation parameters and the heterogeneity of the spiral ganglion cells themselves, which differ in caliber and mediolateral position in the ganglion as well as pathophysiology. Indeed, it is possible that such heterogeneity (or lack of it) is one of the most important factors that determines whether a subject is confused by strong gradients in phase-locking when using low frequency pulsatile strategies. That is, subjects with heterogeneously damaged spinal ganglion cells may have less difficulty with perceptual dissonance and less ability to perceive the effects predicted for the hypothetical experiments described above.

One important and generally overlooked factor is the shape of the potential gradient created across the spiral ganglion, which may account for unexpected results reported for monopolar vs. bipolar channels and single contacts vs. virtual channels. Accurate models of the spread of stimulation current and the initiation of action potentials in spiral ganglion cells are now available. These can be used to identify sets of stimulation patterns that are most likely to produce perceptually compelling effects on the phase-locked pitch decoder. Such patterns can then be administered to cochlear implant patients, using conventional psychophysical testing plus careful assessment of subjective percepts to identify effects on perceived pitch and timbre.

Implications for Cochlear Implant Development

Cochlear implants can be improved by providing more appropriate cues to the actual neural decoder of phase-locked pitch. A more immediately promising tactic may be to weaken the dissonant cues so that they are more easily ignored. This may be the net effect of the recent emphasis on pulse repetition rates that are much higher (>2 kpps) than necessary to avoid spurious rate-pitch sensations (including those that arise from beating of stimulus rates against refractory period. In at least some patients, these benefits appear to outweigh the likely increase in cross-talk (in comparison to the longer duration biphasic pulses that are possible with lower repetition rates and that should produce relatively less rectification and less cross-talk). The beneficial effects of randomization of phase may be difficult to disentangle, however, from other putative benefits of very high frequency stimulus content.

Post-linguistically deafened recipients of a cochlear implant often find it difficult to provide consistent pitch rankings among electrodes, at least initially. Novel stimulation patterns can result in unexpected and distracting senses of pitch that are not predicted from either the place or rate pitch cues inherent in the electrical stimulation parameters (Busby et al., 2003). This may occur if the electrical stimulation results in conflicts among pitch cues that have never before been experienced. If a group of such patients had somewhat different strategies for resolving conflicting cues before they lost their acoustic hearing, then they may differ greatly in the magnitude and nature of the perceptual dissonance that they experience and the speed with which they learn to resolve this dissonance into consistent pitch and speech percepts. Training systems for speech perception may be useful for poor users of cochlear implants, particularly if they are designed to deal with such perceptual dissonance by encouraging subjects to focus on the useful cues and ignore the erroneous ones.

The various embodiments described herein may be constructed with a variety of different computer hardware and/or software within the scope of the cochlear implant devices and methods. The various illustrative logical blocks, modules, and circuits described in connection with the embodiments disclosed herein may be implemented or performed with a general purpose processor, a computer readable medium (i.e. CD, DVD), a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The previous description of the disclosed embodiments is provided to enable any person skilled in the art to make or use the cochlear Implant fitting, methods and systems. Various modifications to these embodiments will be readily apparent to those skilled in the art, and the generic principles defined herein may be applied to other embodiments without departing from the spirit or scope of the devices, methods and systems described herein. Thus, the cochlear Implant fitting, devices, methods and systems are not intended to be limited to the embodiments shown herein but are to be accorded the widest scope consistent with the principles and novel features disclosed herein.

The invention claimed is:

1. A method of identifying which of several speech processing strategies are likely to produce the best results in fitting of a cochlear implant in a patient comprising:
   a) applying a first and then a different second stimulation pattern to an auditory nerve of the patient via the cochlear implant, each stimulation pattern having pulses with a frequency sufficient to prevent phase-locking of auditory nerve activity in the patient, the pulses of at least one of the stimulation patterns being repeatedly interrupted at a rate which is greater than the rate associated with rate pitch sensation but less than the rate limit for phase-locking of the auditory nerve activity;
   b) receiving from the patient information in response to the applied stimulation patterns, wherein the information indicates the sound percepts that the patient has experienced by the applied stimulation patterns; and
   c) identifying which of several speech processing strategies are likely to produce the best results in fitting the cochlear implant in the patient based on the patient information.

2. The method of claim 1 further comprising adjusting the duration of the interruptions.

3. The method of claim 2 further comprising adjusting the amplitudes of the stimulation patterns so as to produce percepts by the patient of equal loudness in each of the applied patterns.

4. The method of claim 1, further comprising applying similar stimulation patterns at the same frequency to two or more electrodes of the cochlear implant at the same time.

5. The method of claim 4, wherein the similar stimulation patterns are applied to each electrode at the same frequency but with different signs and/or amplitudes of stimulation.

6. The method of claim 4, wherein the similar stimulation patterns are applied to each electrode with phase delays between the electrodes.

7. The method of claim 4, wherein the stimulation patterns are applied to each electrode having different stimulus waveforms at each electrode.

8. The method of claim 1, wherein the frequency of stimulation is greater than 4 kpps.

9. The method of claim 1, wherein the interruption durations in the stimulation pattern are less than 3 ms and greater than 0.3 ms.

10. Computer-readable media having instructions stored thereon that, when read by a computer processing system, cause the computer processing system to specify stimulation patterns having the characteristics of the stimulation patterns recited in claim 1.

11. A cochlear implant fitting system for identifying an effective speech processing strategy to produce the best results in a patient comprising:
   a) a processing system configured to receive and process input from a user;
   b) computer-readable instructions in the processing system configured to cause controlling data to be generated by the processing system in response to the input that specifies first and then second stimulation patterns having the characteristics of the stimulation patterns recited in claim 1; and
   e) a controller configured to receive the controlling data and to generate electrical stimulation patterns consistent with the controlling data of a type that is appropriate for delivery to an auditory nerve of the patient via an electrode array.

12. The system of claim 11, wherein the computer-readable instructions are configured to cause the controlling data to adjust the duration of the interruptions.

13. The system of claim 12, wherein the computer-readable instructions are configured to cause the controlling data to adjust the amplitudes of the stimulation patterns so as to produce percepts by the patient of equal loudness in each of the applied patterns.

14. The system of claim 11, wherein the computer-readable instructions are configured to cause the controlling data to specify similar stimulation patterns at the same frequency for application to two or more electrodes of a cochlear implant at the same time.

15. The system of claim 14, wherein the computer-readable instructions are configured to cause the controlling data to specify different signs and/or amplitudes for the stimulation patterns.

16. The system of claim 14, wherein the computer-readable instructions are configured to cause the controlling data to specify phase delays between the stimulation patterns.

17. The system of claim 14, wherein the computer-readable non-transitory instructions are configured to cause the controlling data to specify different stimulation pattern waveforms.

18. The system of claim 11, wherein the computer-readable instructions are configured to cause the controlling data to specify a frequency of stimulation greater than 4 kpps.

19. The system of claim 11, wherein the computer-readable instructions are configured to cause the controlling data to specify that the interruptions in the stimulation pattern are less than 3 ms and greater than 0.3 ms.

20. The method of claim 1 wherein the pulses in one of the stimulation patterns are not interrupted.

21. The system of claim 11 wherein the computer-readable instructions are configured to cause the controlling data to specify that the pulses in one of the stimulation patterns are not interrupted.

22. The system of claim 11 further comprising:
a) an implantable electrode array configured to be implanted in the patient; and
b) a cochlear implant being coupled to the electrode array, configured to be implanted in the patient.

23. The method of claim 1 wherein the pulses of both stimulation patterns are repeatedly interrupted at a rate which is the same for both stimulation patterns, at a rate which is greater than the rate associated with rate pitch sensation but less than the rate limit for phase-locking of the auditory nerve activity, and with a duration to the interruptions which are different for each stimulation pattern.

24. The system of claim 11 wherein the first and then second stimulation patterns have the characteristics of the stimulation patterns recited in claim 23.

* * * * *